(12) United States Patent
Hsu

(10) Patent No.: US 9,162,363 B2
(45) Date of Patent: Oct. 20, 2015

(54) CUTTER WITH A SLIDER THAT CAN BE PUSHED FROM TWO DIRECTIONS AND SLIDER FOR THE SAME

(71) Applicant: SDI CORPORATION, Chang Hua (TW)

(72) Inventor: Chih-Wei Hsu, Chang Hua (TW)

(73) Assignee: SDI Corporation, Chang Hua (TW)

( * ) Notice: Subject to any disclaimer, the term of this patent is extended or adjusted under 35 U.S.C. 154(b) by 228 days.

(21) Appl. No.: 13/771,263

(22) Filed: Feb. 20, 2013

(65) Prior Publication Data

US 2014/0041235 A1  Feb. 13, 2014

(30) Foreign Application Priority Data

Aug. 7, 2012 (TW) .............................. 101128410 A

(51) Int. Cl.
| | |
|---|---|
| *B26B 1/08* | (2006.01) |
| *B26B 27/00* | (2006.01) |
| *B26B 5/00* | (2006.01) |
| *B26B 1/10* | (2006.01) |
| *B26B 1/04* | (2006.01) |
| *A61B 17/3211* | (2006.01) |

(52) U.S. Cl.
CPC ... *B26B 1/08* (2013.01); *B26B 1/04* (2013.01); *B26B 1/10* (2013.01); *B26B 5/001* (2013.01); *B26B 5/002* (2013.01); *B26B 5/003* (2013.01); *B26B 5/005* (2013.01); *B26B 27/005* (2013.01); *A61B 2017/32113* (2013.01)

(58) Field of Classification Search
CPC .......... B26B 5/003; B26B 5/001; B26B 1/08; B26B 5/005; B26B 1/10; B26B 1/04; B26B 27/005; A61B 2017/32113

USPC ........................................ 30/2, 151, 162, 164
See application file for complete search history.

(56) References Cited

U.S. PATENT DOCUMENTS

| | | | |
|---|---|---|---|
| 4,735,202 A * | 4/1988 | Williams | ...................... 606/167 |
| 5,502,896 A | 4/1996 | Chen | |
| 2009/0313836 A1 | 12/2009 | Wei | |
| 2011/0308092 A1* | 12/2011 | Lin | ................................ 30/164 |

FOREIGN PATENT DOCUMENTS

| | | | |
|---|---|---|---|
| CN | 101269491 A | | 9/2008 |
| DE | 202004009884 U1 | | 9/2004 |
| EP | 2433762 | * | 3/2012 |
| EP | 2433762 A1 | * | 3/2012 |
| FR | 2874346 | * | 2/2006 |
| FR | 2874346 A3 | * | 2/2006 |
| TW | 281141 | * | 7/1996 |
| TW | M390212 | | 10/2010 |

* cited by examiner

*Primary Examiner* — Ned Landrum
*Assistant Examiner* — Liang Dong
(74) *Attorney, Agent, or Firm* — Alan D. Kamrath; Kamrath IP Lawfirm, P.A.

(57) ABSTRACT

A cutter with a slider that can be pushed from two directions has a housing, a blade holder, a slider, and a blade. The slider is mounted moveably on the housing, is connected to the blade holder, and has an upper sliding element, a lower sliding element, and a resilient tab engaging at least one tooth formed on the blade holder. The upper sliding element has an L-shaped cross section to form a top wall and a side wall corresponding respectively to a top wall and a side wall of the housing. A guiding recess is defined by the side wall of the upper sliding element to slidably receive a portion of the side wall of the housing that forms an edge of a guiding channel. Accordingly, the cutter is convenient in use.

24 Claims, 7 Drawing Sheets

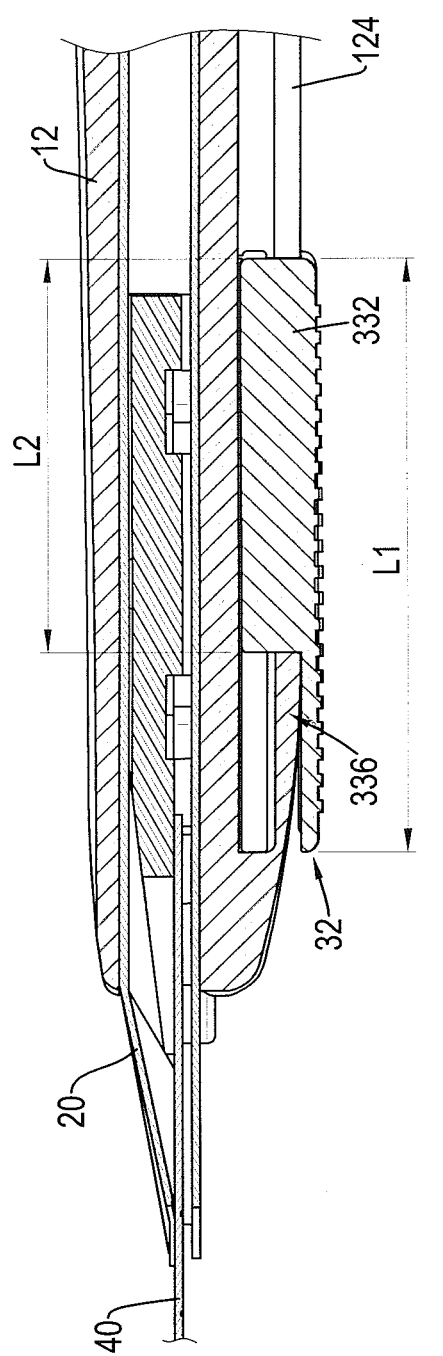

CUTTER WITH A SLIDER THAT CAN BE PUSHED FROM TWO DIRECTIONS AND SLIDER FOR THE SAME

BACKGROUND OF THE INVENTION

1. Field of the Invention

The present invention relates to a cutter and, more particularly, to a cutter having a slider that can be pushed from two directions.

2. Description of Related Art

A cutter is widely used to cut paper or the like and comprises a blade holder, a blade, and a slider. The blade is mounted slidably in the blade holder. The slider is mounted slidably on the blade holder and is connected to the blade to push the blade out from the blade holder by different desired lengths to fit with different working needs. Taiwan Utility Model No. M390212, entitled "Slider For a Cutter," discloses a slider slidably mounted in a blade holder and connected with a blade. The slider of the '212 Patent comprises an upper sliding element, a lower sliding element, and a resilient tab. A combining tab and a combining slot are formed respectively on the upper and lower sliding elements and engaged with each other to combine the upper and lower sliding elements with each other. The upper sliding element is slidably mounted in a guiding channel defined in a side wall of the blade holder and is exposed from the guiding channel. Accordingly, when the upper sliding element is pushed, the blade can be extended out from or retracted into the blade holder, and the movement of the blade is controlled.

However, the upper sliding element of the conventional slider, such as that shown in the '212 Patent, is substantially a flat board, so the upper sliding element only has a single pushed surface that is pushed by a user. Therefore, the slider can only be pushed from a single direction, such that to push the slider to move, the user has to hold the cutter with a specific holding manner and push the slider from a specific direction. Therefore, the use of the slider is not versatile and convenient. In addition, the guiding channel of a cutter as described in the '212 Patent is usually formed in a middle portion of the side wall of the blade holder and has a wide width. External objects easily enter into the blade holder via the guiding channel, impairing the smooth operation of the cutter.

Taiwan Utility Model No. 281141, entitled "Cutter with Easily Detachable Structure for Replacing Blade," discloses a pushing slider having an L-shaped cross section to enable the slider to be pushed from two directions. However, the slider of the '141 Patent is formed as a single piece and cannot hold a cutter in position. The user has to keep pushing the slider for keeping the blade at an extending position for cutting, so the operation of the cutter of the '141 Patent is not convenient.

China Patent Publication No. 101269491, entitled "Cutting Knife," comprises a slider having a complicated structure, and the slider of the '491 Patent is pushed only from a single specific direction.

To overcome the shortcomings, the present invention provides a cutter and a slider for the same to mitigate or obviate the aforementioned problems.

SUMMARY OF THE INVENTION

The main objective of the invention is to provide a cutter with a slider that can be pushed from two directions to improve convenience and versatility in use.

The cutter has a housing, a blade holder, a slider, and a blade. The housing has a body and a guiding channel. The body is hollow and has a top wall and a side wall. The guiding channel is defined through the side wall of the body and has an edge. The blade holder is disposed in the body of the housing and has multiple teeth. The slider is mounted moveably on the housing, is connected to the blade holder, and has an upper sliding element, a lower sliding element, and a resilient tab. The upper sliding element has an L-shaped cross section to form a top wall and a side wall corresponding respectively to the top wall and the side wall of the body of the housing. A guiding recess is defined by the side wall of the upper sliding element and slidably receives a portion of the side wall of the body of the housing that forms the edge of the guiding channel. The lower sliding element is combined with the upper sliding element. The resilient tab is mounted on the lower sliding element and engages at least one of the teeth on the blade holder. The blade is connected with the slider and is mounted moveably in the blade holder.

The present invention further provides a slider having an upper sliding element, a lower sliding element, and a resilient tab. The upper sliding element has an L-shaped cross section to form a top wall and a side wall, a positioning member, and a guiding recess. The positioning member is formed on and protrudes from an inner surface of the side wall of the upper sliding element. The guiding recess is defined between the side wall of the upper sliding element and the positioning member and is adapted to slidably receive a portion of a side wall of a body of a housing of the cutter that forms an edge of a guiding channel defined in the side wall of the body of the housing. The lower sliding element is combined with the upper sliding element. The resilient tab is mounted on the lower sliding element.

The cutter with the slider in accordance with the present invention can achieve the following advantages.

1. With the L-shaped cross section of the upper sliding element, the upper sliding element can be pushed to move along the guiding channel in the body from the top wall, the side wall or the conjunction segment between the top wall and the side wall of the upper sliding element for controlling and auto-locking the extension length of the cutter. Pushing the slider is not limited by a single specific direction or a single pushed surface, and the use of the cutter is convenient.

2. The width of the guiding channel in the housing can be reduced to keep the internal structures of the cutter from being exposed. External objects can be kept from entering into the housing to prevent the operation of the cutter from being interfered, and the appearance of the cutter is esthetic to increase the attraction to consumers.

3. The positioning member and the connecting base can provide an L-shaped abutment relationship between the upper sliding element and the lower sliding element. Accordingly, the structural stability of the combination of the upper and lower sliding elements can be enhanced, and the slider can be pushed to move and to operate.

4. The upper sliding element further has two protrusions having pushing blocks to abut the middle positions of legs of the resilient tab. Therefore, the contact area between the upper sliding element and the resilient tab and the pushing force from the upper sliding element to the resilient tab can be increased. The resilient tab can be pushed to disengage from the teeth.

5. An escaping gap is formed between the upper sliding element and the positioning member, such that the moving travel of the upper sliding element relative to the guiding channel can be prolonged. Consequently, the extension length of the blade extending out of the housing can also be prolonged to fit with different needs of uses. The cutter is versatile in use with enhanced practical utility.

Other objectives, advantages and novel features of the invention will become more apparent from the following detailed description when taken in conjunction with the accompanying drawings.

BRIEF DESCRIPTION OF THE DRAWINGS

FIG. 7 is an enlarged cross sectional top view of the cutter in FIG. 1.

DETAILED DESCRIPTION OF PREFERRED EMBODIMENTS

Figure 1:
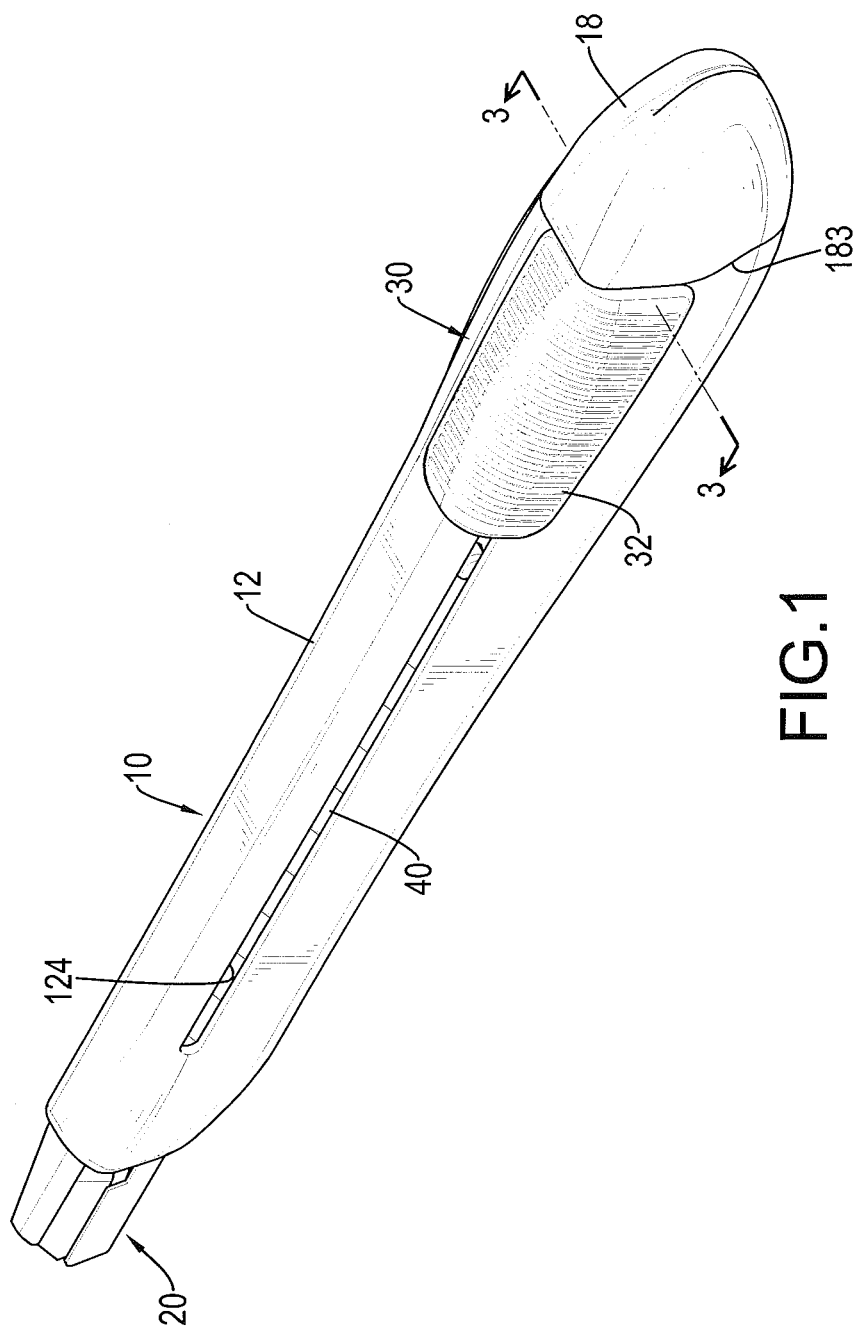
FIG. 1 is a perspective view of a cutter with a slider in accordance with the present invention.
Figure 2:
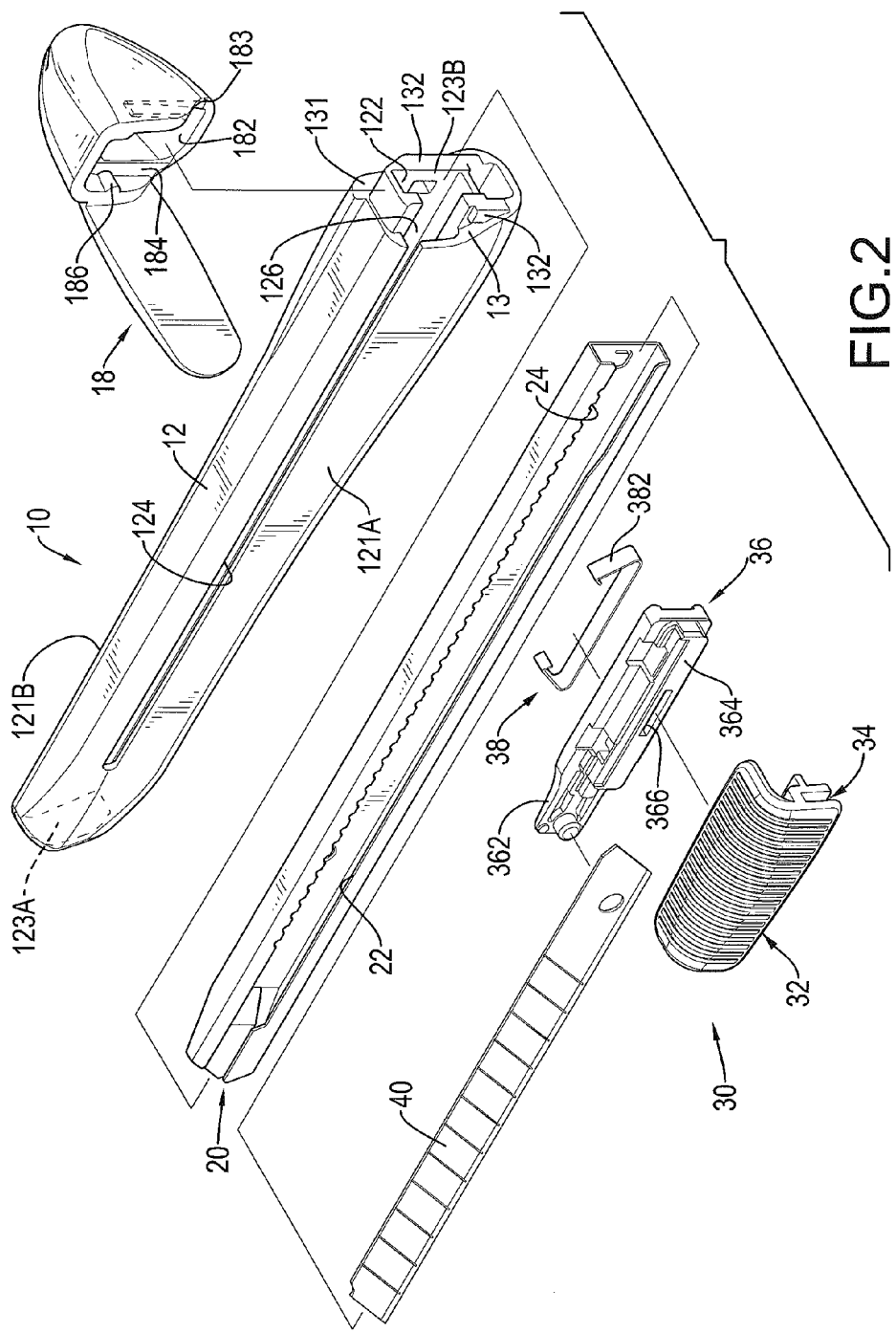
FIG. 2 is an exploded perspective view of the cutter with the slider in FIG. 1.
Figure 3:
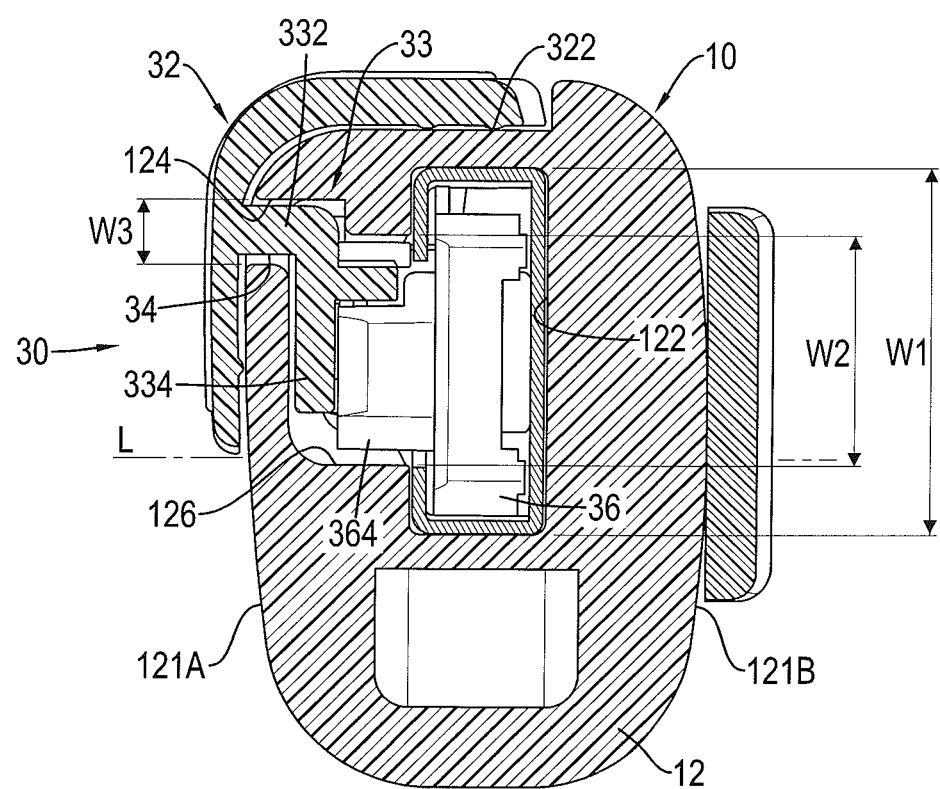
FIG. 3 is an enlarged end view in partial section of the cutter with the slider along line 3-3 in FIG. 1.

With reference to FIGS. 1 and 2, a cutter in accordance with the present invention comprises a housing 10, a blade holder 20, a slider 30, and a blade 40. The housing 10 may be plastic. With further reference to FIG. 3, the housing 10 comprises a hollow body 12 and a rear cap 18. The body 12 has a top wall, first and second side walls 121A, 121B, a chamber 122, first and second openings 123A, 123B, a guiding channel 124, and a passage 126. The chamber 122 is elongated and is defined longitudinally in the body 12. The first and second openings 123A, 123B are defined respectively in a front end and a rear end of the body 12 and communicate with the chamber 122. The guiding channel 124 is longitudinally defined through one of the side walls 121A of the body 12 and has an edge. The side wall 121A of the body 12 in which the guiding channel 124 is defined is defined as a first side wall, and the other side wall 121B is defined as a second side wall. The guiding channel 124 is located above a central line L that is defined in a longitudinal direction of the first side wall 121A of the body 12, and the guiding channel 124 is adjacent to the top wall of the body 12. The central line L divides the first side wall 121A of the body 12 substantially evenly into an upper segment and a lower segment. The guiding channel 124 has a rear end communicating with the second opening 123B in the rear end of the body 12 and a front end spaced from and being free from communicating with the first opening 123A in the front end of the body 12. The passage 126 is elongated, is longitudinally defined in the body 12, and is located between and communicating with the guiding channel 124 and the chamber 122. Accordingly, the guiding channel 124 communicates with the chamber 122 via the passage 126. Preferably, the passage 126 has a width W2 smaller than a width W1 of the chamber 122 and larger than a width W3 of the guiding channel 124 as shown in FIG. 3.

Figure 4:
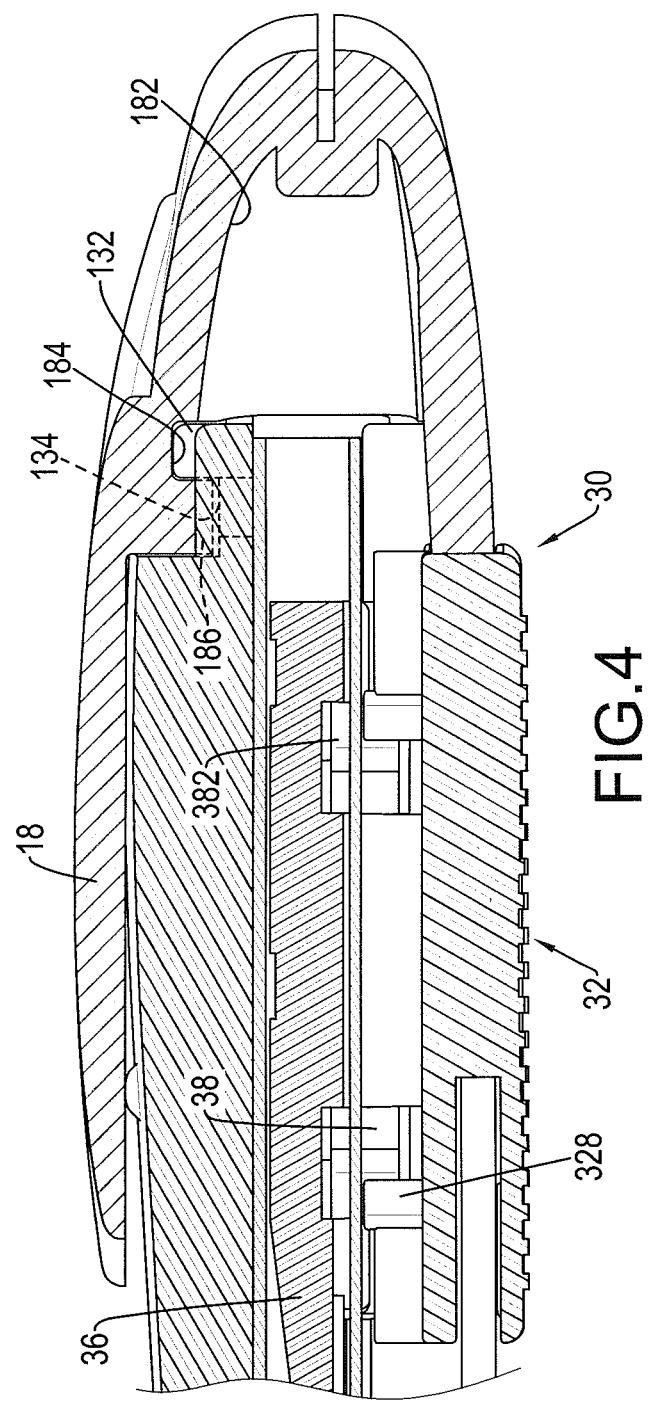
FIG. 4 is an enlarged top view in partial section of the cutter in FIG. 1.

The rear cap 18 is attached to the rear end of the body 12 to close the second opening 123B in the rear end of the body 12. With reference to FIGS. 1, 2, and 4, the rear cap 18 can be combined with the body 12 in a longitudinal direction or in a non-longitudinal direction. In the longitudinal direction, the rear cap 18 is combined with the body 12 along a longitudinal direction of the body 12 as in the '212 Patent or the '491 Patent. In the non-longitudinal direction, the rear cap 18 is combined with the body 12 along a direction that is not the longitudinal direction of the body 12. When the rear cap 18 is combined with the body 12 in a non-longitudinal direction, each side wall 121A, 121B of the body 12 has a combining recess 13, 131 defined in the side wall 121A, 121B at the rear end of the body 12, extending from the top wall to a position near a bottom wall of the body 12, and spaced from the bottom wall of the body 12. Each combining recess 13, 131 has a concave bottom. Each combining recess 13, 131 further has a combining rib 132 formed on the concave bottom of the combining recess 13, 131. Preferably, the combining recess 13 defined in the first side wall 121A of the body 12 is defined as a first combining recess 13, and the combining recess 131 defined in the second side wall 121B of the body 12 is defined as a second combining recess 131. The first combining recess 13 communicates with the rear end of the guiding channel 124 and the passage 126. The second combining recess 131 further has an engaging recess 134 defined in a bottom surface of the second combining recess 131. The rear cap 18 is hollow and has a holding recess 182. The holding recess 182 is defined in the rear cap 18 and holds the rear end of the body 12 inside. The rear cap 18 has an edge having a shape corresponding to and matching the concave bottoms of the combining recesses 13, 131 in the body 12 to form two cut-off sections 183 respectively in ends of the edge of the rear cap 18. The rear cap 18 further has two engaging grooves 184 defined respectively in two inner surfaces of the holding recess 182 in the rear cap 18 and respectively engaging the combining ribs 132 on the combining recesses 13,131. The rear cap 18 further has an engaging block 186 formed on and protruding from one of the inner surfaces of the holding recess 182 of the rear cap 18 and engaging the engaging recess 134 in the body 12. With the corresponding shapes of the combining recesses 13, 131 in the body 12 and the cut-off sections 183 in the rear cap 18, the rear cap 18 is combined with the rear end of the body 12 along a direction from the top wall to the bottom wall of the body 12. The combining direction of the rear cap 18 is different from the longitudinal direction of a conventional rear cap to provide another combination manner for the rear cap 18 and the body 12. In addition, with the engagements between the engaging recess 134 and the engaging block 186 and between the combining ribs 132 and the engaging grooves 184, the combination of the rear cap 18 with the body 12 is firm.

With reference to FIGS. 1 to 3, the blade holder 20 is mounted in the chamber 122 in the body 12. The blade holder 20 is elongated and hollow and has a front end extending out of the first opening 123A in the front end of the body 12. The blade holder 20 has an elongated positioning channel 22 defined in a side wall of the blade holder 20 facing the first side wall 121A of the body 12 in which the guiding channel 124 is defined. Multiple teeth 24 are formed along an inner edge of the positioning channel 22.

Figure 5:
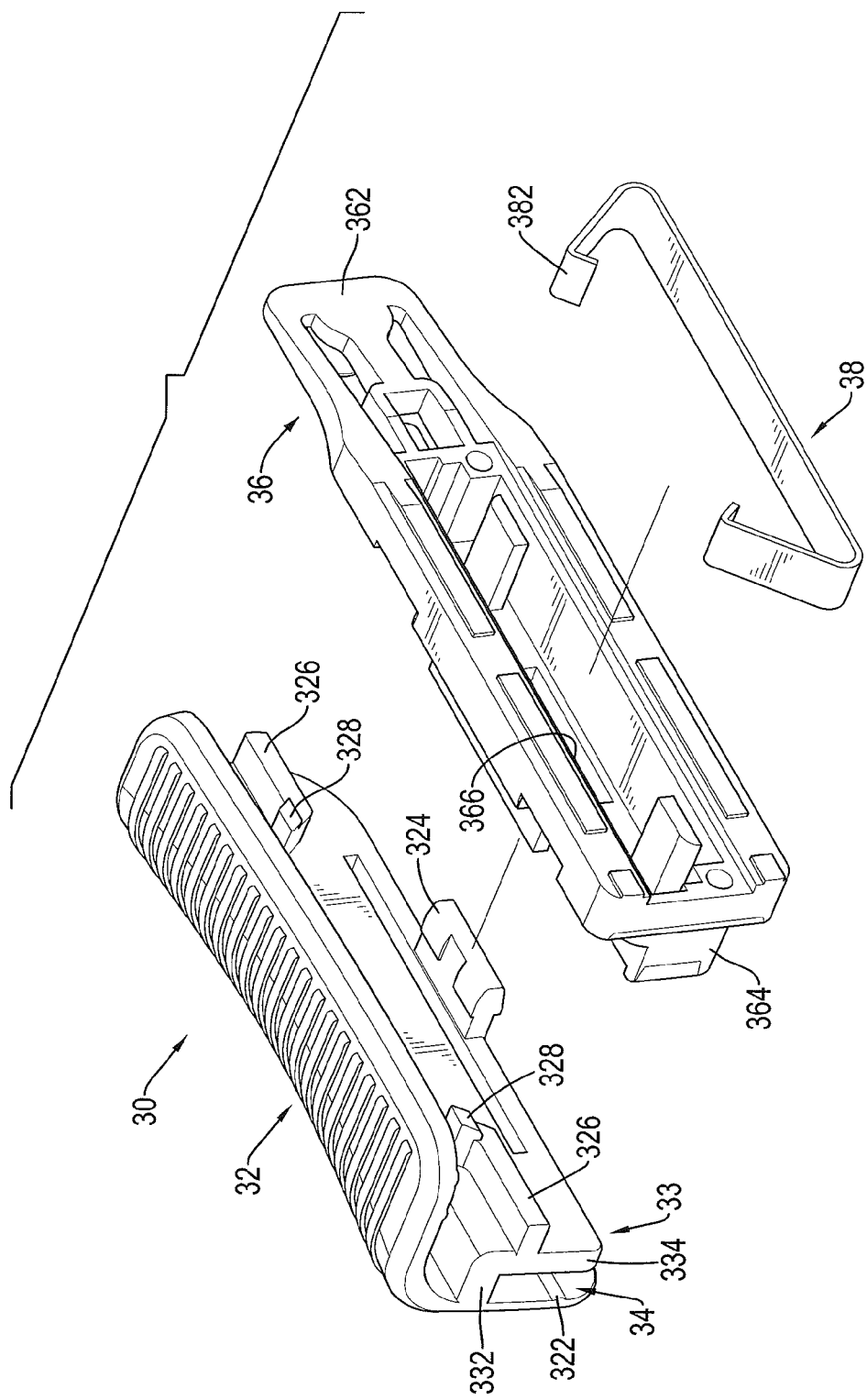
FIG. 5 is an enlarged exploded perspective view of the slider in FIG. 1.

The slider 30 is mounted moveably on the housing 10, is connected to the blade holder 20, and comprises an upper sliding element 32, a lower sliding element 36, and a resilient tab 38. With reference to FIGS. 2, 3, and 5, the upper sliding element 32 has an L-shaped cross section to form a top wall and a side wall corresponding respectively to the top wall and the first side wall 121A of the body 12. The upper sliding element 32 has a concave conjunction segment formed between the top wall and the side wall of the upper sliding element 32. A positioning member 33 is formed on and protrudes from the side wall of the upper sliding element 32 at an inner surface facing the housing 10. The positioning member 33 has an L-shaped cross section and comprises a lateral segment 332 and a mounting segment 334. The lateral segment 332 is connected with the side wall of the upper sliding element 32 and slidably mounted in the guiding channel 124. The mounting segment 334 is connected with an end of the lateral segment 332 and is substantially parallel with the side wall of the upper sliding element 32 to define a guiding recess 34 between the mounting segment 334 and the side wall of the upper sliding element 32. The guiding recess 34 slidably receives a portion of the side wall of the body 12 that forms the edge of the guiding channel 124. With the arrangement of the guiding recess 34, the upper sliding element 32 can slide relative to and along the guiding channel 124 smoothly and stably. In addition, two ribs 322 with smooth outer surfaces are formed on the upper sliding element 32, and the two ribs 322 are formed respectively on the top wall and the side wall of the upper sliding element 32 at sides facing the housing 10 and respectively abutting the top wall and the first side wall 121A of the body 12. With the smooth outer surfaces of the ribs 322, the movement of the upper sliding element 32 relative to the guiding channel 124 is smooth.

The lower sliding element 36 is combined with the upper sliding element 32 and is slidably mounted in the blade holder 20. The lower sliding element 36 has a blade mount 362 extending from one end of the lower sliding element 36 and connected with the blade 40. The lower sliding element 36 further has a connecting base 364 formed on and protruding from the lower sliding element 36 at a side facing the upper sliding element 32. The connecting base 364 extends out of the positioning channel 22 in the blade holder 20 and is slidably mounted in the passage 126 in the body 12. The connecting base 364 is connected with the upper sliding element 32 to enable the lower sliding element 36 to move with the upper sliding element 32 relative to the blade holder 20. Preferably, the upper sliding element 32 has a combining tab 324 formed on the upper sliding element 32, and the connecting base 364 has a combining slot 366 defined in the connecting base 364 and engaging the combining tab 324 on the upper sliding element 32. With engagement between the combining tab 324 and the combining slot 366, the upper sliding element 32 and the lower sliding element 36 are combined with each other. Preferably, the combining tab 324 can be formed on the side wall of the upper sliding element 32 or can be formed on the mounting segment 334 of the positioning member 33. The mounting segment 334 of the positioning member 33 abuts the side of the connecting base 364 facing the upper sliding element 32.

Figure 6:
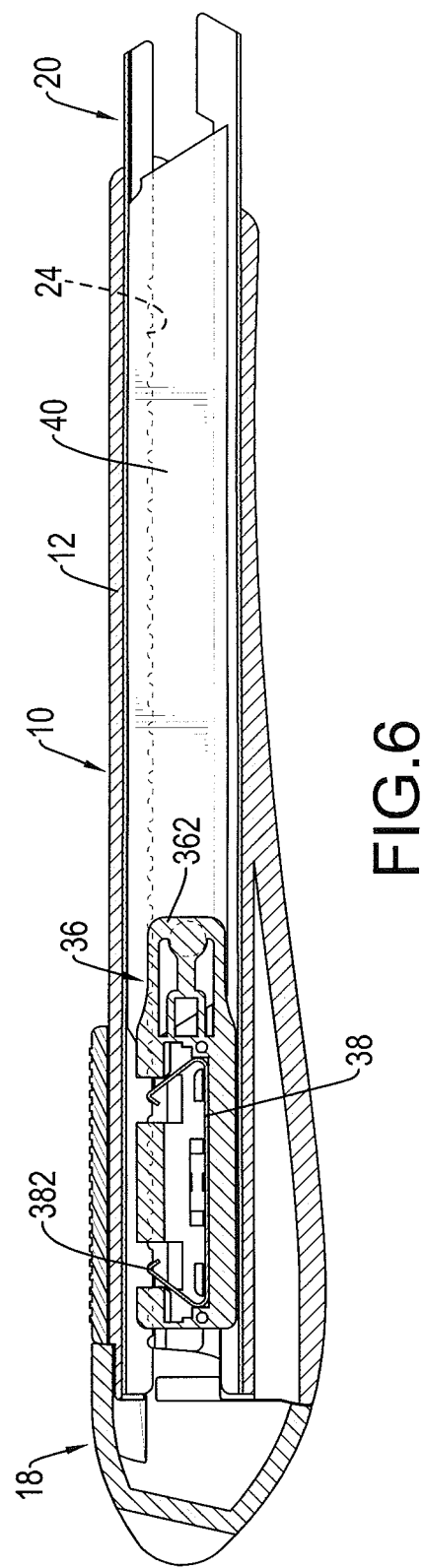
FIG. 6 is a side view of a partial section of the cutter in FIG. 1.

With reference to FIGS. 4 and 6, a resilient tab 38 is resilient and is mounted and positioned in the lower sliding element 36. The resilient tab 38 has two legs 382 protruding inward from two ends of the resilient tab 38 and extending out of the lower sliding element 36. Each leg 382 of the resilient tab 38 has an engaging end extending out from the lower sliding element 36 and engaging one of the teeth 24 on the blade holder 20. The engaging ends of the legs 382 may be curved, and may extend out from a top surface of the connecting base 364 of the lower sliding element 36. The upper sliding element 32 further has two protrusions 326 abutting respectively the engaging ends of the legs 382 of the resilient tab 38. Each protrusion 326 has an inclined pushing surface defined in an end of the protrusion 326 and abutting a corresponding one of the legs 382 of the resilient tab 38. Preferably, the protrusions 326 are laterally formed on and protrude from the mounting segment 334 of the positioning member 33 and abut the top surface of the connecting base 364 on the lower sliding element 36. Accordingly, the protrusions 326 can push against the engaging ends of the legs 382 to disengage the engaging ends of the legs 382 from the teeth 24. With the abutments between the protrusions 326 and the top surface of the connecting base 364 and between the mounting segment 334 and the side of the connecting base 364, an L-shaped abutment relationship between the positioning member 33 and the connecting base 364 is provided to enhance the structural stability of the combination of the upper sliding element 32 and the lower sliding element 36. Furthermore, each protrusion 326 further has a pushing block 328 formed on the protrusion 326 at the end facing each other. The pushing block 328 of each protrusion 326 has a length protruding from the upper sliding element 32 toward the lower sliding element 36, and said length of the pushing block 328 is larger than a length of the protrusion 326 protruding from the upper sliding element 32 toward the lower sliding element 36. Accordingly, each pushing block 328 extends to abut a middle position of the engaging end of a corresponding one of the legs 382 of the resilient tab 38, such that the contact area where the upper sliding element 32 pushes the legs 382 can be enlarged, and the pushing force for pushing the legs 382 can also be increased.

With reference to FIGS. 1 and 6, after the slider 30 is assembled on the housing 10 and the blade holder 20, the top wall and the side wall of the upper sliding element 32 correspond respectively to the top wall and the first side wall 121A of the body 12. When a user holds the housing 10, the user can push the top wall, the side wall or the conjunction segment of the upper sliding element 32 to move the upper sliding element 32 relative to and along the guiding channel 124 in the body 12. Consequently, the blade 40 connected with the lower sliding element 36 can be extended out from or retracted into the first opening 123A in the front end of the housing 10. With the engagement between the legs 382 of the resilient tab 38 and the teeth 24 on the blade holder 20, the blade 40 can be held at a position where a desired extension length extends out from the body 12. Therefore, the slider 30, not limited by a single specific direction or pushed face, can be pushed from different directions, and the cutter is versatile in use with enhanced convenience.

In addition, the width W3 of the guiding channel 124 can be adjustably reduced, such that the internal structure of the cutter can be kept from being exposed. The external objects can be kept from entering into the housing 10 to prevent the operation of the cutter from being interfered with, and the appearance of the cutter is esthetic to increase the attraction to consumers.

With reference to FIG. 7, the lateral segment 332 of the positioning member 33 has a length L2 smaller than a length L1 of the upper sliding element 32 to define an escaping gap 336 between the positioning member 33 and the top wall and the side wall of the upper sliding element 32. With the arrangement of the escaping gap 336 formed between the upper sliding element 32 and the positioning member 33, the moving travel of the upper sliding element 32 relative to the guiding channel 124 can be prolonged. Consequently, the extension length of the blade 40 extending out of the housing 10 can also be prolonged to fit with different needs of uses. The cutter is versatile in use with enhanced practical utility.

Even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A cutter comprising:
 a housing having:
  a hollow body having a top wall and a side wall; and
  a guiding channel defined through the side wall of the body and having an edge;
 a blade holder disposed in the body of the housing and having multiple teeth;
 a slider mounted moveably on the housing, connected to the blade holder, and comprising:
  an upper sliding element having:
   an L-shaped cross section to form a top wall and a side wall corresponding respectively to the top wall and the side wall of the body of the housing;
   two protrusions; and
   a guiding recess defined by the side wall of the upper sliding element and slidably receiving a portion of the side wall of the body of the housing that forms the edge of the guiding channel;
  a lower sliding element combined with the upper sliding element and comprising a connecting base formed on and protruding from the lower sliding element at a side facing the upper sliding element;
  a resilient tab mounted on the lower sliding element and engaging at least one of the teeth on the blade holder; and
 a blade connected with the slider and mounted moveably in the blade holder, wherein:
  the two protrusions abut a top surface of the connecting base on the lower sliding element;
  the resilient tab has two legs protruding from two ends of the resilient tab and extending out of the lower sliding element;
  each leg of the resilient tab has an engaging end extending out from the lower sliding element and engaging one of the multiple teeth on the blade holder;
  the two-protrusions of the upper sliding element abut respectively the engaging ends of the two legs of the resilient tab
  the two protrusions are laterally formed on and protrude from the mounting segment of the positioning member; and
  each protrusion has an inclined pushing surface defined in an end of the protrusion and abutting a corresponding one of the two legs of the resilient tab;
  each protrusion further has a pushing block formed on the protrusion at the end in which the inclined pushing surface is defined and faces the other protrusion; and
  the pushing block of each protrusion has a length protruding from the upper sliding element toward the lower sliding element and that is larger than a length of each protrusion protruding from the upper sliding element toward the lower sliding element.

2. The cutter as claimed in claim 1, wherein:
 the body of the housing has a first side wall in which the guiding channel is defined and a second side wall;
 each side wall of the body has a combining recess defined in the side wall at the rear end of the body and extending from the top wall to a position near a bottom wall of the body and spaced from the bottom wall of the body;
 each combining recess has a concave bottom; and
 the housing further has a rear cap which is hollow, attached to the rear end of the body and having:
  a holding recess defined in the cap and holding the rear end of the body of the housing inside; and
  an edge having a shape corresponding to and matching the concave bottoms of the combining recesses in the body of the housing to form two cut-off sections respectively in ends of the edge of the rear cap.

3. The cutter as claimed in claim 2, wherein:
 each combining recess of the body of the housing further has a combining rib formed on the concave bottom of the combining recess; and
 the rear cap further has two engaging grooves defined respectively in two inner surfaces of the holding recess in the rear cap and respectively engaging the combining ribs on the combining recesses.

4. The cutter as claimed in claim 3, wherein:
 the body of the housing has an engaging recess defined in the second side wall; and
 the rear cap further has an engaging block formed on and protruding from one of the inner surfaces of the holding recess of the rear cap and engaging the engaging recess in the body of the housing.

5. A cutter comprising:
 a housing having:
  a hollow body having a top wall and a side wall; and
  a guiding channel defined through the side wall of the body and having an edge;
 a blade holder disposed in the body of the housing and having multiple teeth;
 a slider mounted moveably on the housing, connected to the blade holder, and comprising:
  an upper sliding element having:
   an L-shaped cross section to form a top wall and a side wall corresponding respectively to the top wall and the side wall of the body of the housing;
   two protrusions; and
   a guiding recess defined by the side wall of the upper sliding element and slidably receiving a portion of the side wall of the body of the housing that forms the edge of the guiding channel;
  a lower sliding element combined with the upper sliding element and comprising a connecting base formed on and protruding from the lower sliding element at a side facing the upper sliding element;
  a resilient tab mounted on the lower sliding element and engaging at least one of the teeth on the blade holder; and
 a blade connected with the slider and mounted moveably in the blade holder, wherein:
  the two protrusions abut a top surface of the connecting base on the lower sliding element;
  the side wall of the body of the housing has a central line defined in a longitudinal direction of the side wall of the body; and
  the guiding channel is located above the central line;
  the body of the housing further has:
   an elongated chamber defined longitudinally in the body;
   two openings defined respectively in a front end and a rear end of the body and communicating with the chamber; and
   an elongated passage defined in the body and located between and communicating with the guiding channel and the chamber;
  the blade holder is mounted in the chamber; and
  the connecting base of the lower sliding element is mounted slidably in the passage.

6. The cutter as claimed in claim 5, wherein:
the upper sliding element further has a positioning member formed on and protruding from the side wall of the upper sliding element at an inner surface facing the housing; and
the positioning member has an L-shaped cross section and comprises:
a lateral segment connected with the side wall of the upper sliding element and slidably mounted in the guiding channel in the body of the housing; and
a mounting segment connected with an end of the lateral segment and substantially parallel with the side wall of the upper sliding element to define the guiding recess between the mounting segment and the side wall of the upper sliding element.

7. The cutter as claimed in claim 6, wherein the lateral segment of the positioning member has a length smaller than a length of the upper sliding element to define an escaping gap between the positioning member and the top wall and the side wall of the upper sliding element.

8. The cutter as claimed in claim 7, wherein the upper sliding element has a concave conjunction segment formed between the top wall and the side wall of the upper sliding element.

9. The cutter as claimed in claim 8, wherein the upper sliding element further has two ribs with smooth outer surfaces formed on the upper sliding element, wherein the two ribs are formed respectively on the top wall and the side wall of the upper sliding element at sides facing the housing and respectively abutting the top wall and the side wall of the body of the housing.

10. The cutter as claimed in claim 9, wherein:
the lower sliding element further has a combining slot defined in the connecting base;
the upper sliding element further has a combining tab formed on the upper sliding element and engaging the combining slot in the connecting base.

11. The cutter as claimed in claim 10, wherein:
the combining tab is formed on the mounting segment of the positioning member; and
the mounting segment of the positioning member abuts the side of the lower sliding element facing the upper sliding element.

12. The cutter as claimed in claim 11, wherein:
the resilient tab has two legs protruding from two ends of the resilient tab and extending out of the lower sliding element;
each leg of the resilient tab has an engaging end extending out from the lower sliding element and engaging one of the multiple teeth on the blade holder; and
the two-protrusions of the upper sliding element abut respectively the engaging ends of the two legs of the resilient tab.

13. The cutter as claimed in claim 12, wherein:
the two protrusions are laterally formed on and protrude from the mounting segment of the positioning member; and
each protrusion has an inclined pushing surface defined in an end of the protrusion and abutting a corresponding one of the two legs of the resilient tab.

14. The cutter as claimed in claim 5, wherein the passage has a width smaller than a width of the chamber and larger than a width of the guiding channel.

15. The cutter as claimed in claim 14, wherein:
the body of the housing has two side walls including a first side wall in which the guiding channel is defined and a second side wall;
each side wall of the body has a combining recess defined in the side wall at the rear end of the body and extending from the top wall to a position near a bottom wall of the body and spaced from the bottom wall of the body;
each combining recess has a concave bottom; and
the housing further has a rear cap which is hollow, attached to the rear end of the body and having:
a holding recess defined in the rear cap and holding the rear end of the body of the housing inside; and
an edge having a shape corresponding to and matching the concave bottoms of the combining recesses in the body of the housing to form two cut-off sections respectively in ends of the edge of the rear cap.

16. The cutter as claimed in claim 15, wherein:
each combining recess of the body of the housing further has a combining rib formed on the concave bottom of the combining recess; and
the rear cap further has two engaging grooves defined respectively in two inner surfaces of the holding recess in the rear cap and respectively engaging the combining ribs on the combining recesses.

17. The cutter as claimed in claim 16, wherein:
the body of the housing has an engaging recess defined in the second side wall; and
the rear cap further has an engaging block formed on and protruding from one of the inner surfaces of the holding recess of the rear cap and engaging the engaging recess in the body of the housing.

18. A slider for a cutter comprising:
an upper sliding element having:
an L-shaped cross section to form a top wall and a side wall;
a positioning member formed on and protruding from an inner surface of the side wall of the upper sliding element;
a guiding recess defined between the side wall and the positioning member and adapted to slidably receive a portion of a side wall of a body of a housing of the cutter that forms an edge of a guiding channel defined in the side wall of the body of the housing; and
two protrusions;
a lower sliding element combined with the upper sliding element and comprising a connecting base formed on and protruding from the lower sliding element at a side facing the upper sliding element; and
a resilient tab mounted on the lower sliding element, wherein:
the two protrusions abut a top surface of the connecting base on the lower sliding element;
the resilient tab has two legs protruding from two ends of the resilient tab and extending out of the lower sliding element;
each leg of the resilient tab has an engaging end extending out from the lower sliding element; and
the two-protrusions of the upper sliding element abut respectively the engaging ends of the two legs of the resilient tab;
each protrusion has an inclined pushing surface defined in an end of the protrusion and abutting a corresponding one of the two legs of the resilient tab; and
each protrusion further has a pushing block formed on the protrusion at the end in which the inclined pushing surface is defined and faces the other protrusion and abutting a middle position of the engaging end of a corresponding one of the two legs of the resilient tab.

19. The slider as claimed in claim 18, wherein the positioning member has an L-shaped cross section and comprises:
   a lateral segment connected with the side wall of the upper sliding element; and
   a mounting segment connected with an end of the lateral segment and substantially parallel with the side wall of the upper sliding element to define the guiding recess between the mounting segment and the side wall of the upper sliding element.

20. The slider as claimed in claim 19, wherein the lateral segment of the positioning member has a length smaller than a length of the upper sliding element to define an escaping gap between the positioning member and the top wall and the side wall of the upper sliding element.

21. The slider as claimed in claim 20, wherein the upper sliding element has a concave conjunction segment formed between the top wall and the side wall of the upper sliding element.

22. The slider as claimed in claim 21, wherein:
the upper sliding element further has two ribs with smooth outer surfaces formed on the upper sliding element; and
the two ribs are formed respectively on the top wall and the side wall of the upper sliding element.

23. The slider as claimed in claim 22, wherein:
the lower sliding element further has a combining slot defined in the connecting base; and
the upper sliding element further has a combining tab formed on the upper sliding element and engaging the combining slot in the connecting base.

24. The slider as claimed in claim 23, wherein:
the combining tab is formed on the mounting segment of the positioning member; and
the mounting segment of the positioning member abuts the side of the lower sliding element facing the upper sliding element.

* * * * *